US006627639B2

United States Patent
Stack et al.

(10) Patent No.: US 6,627,639 B2
(45) Date of Patent: Sep. 30, 2003

(54) USES FOR INDOLETETRAHYDROPYRIDINE DERIVATIVES OF 2,3-DIHYDRO-7H-[1,4] DIOXINO-[2,3-E]INDOLE

(75) Inventors: Gary P. Stack, Ambler, PA (US); Megan Tran, Hoboken, NJ (US); Byron A. Bravo, Eagleville, PA (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 10/339,511

(22) Filed: Jan. 9, 2003

(65) Prior Publication Data
US 2003/0134870 A1 Jul. 17, 2003

Related U.S. Application Data

(63) Continuation-in-part of application No. 10/131,339, filed on Apr. 24, 2002.
(60) Provisional application No. 60/286,575, filed on Apr. 26, 2001.

(51) Int. Cl.[7] ............................................. A61K 31/4433
(52) U.S. Cl. ........................................ 514/300; 514/338
(58) Field of Search .................................. 514/338, 300

(56) References Cited

U.S. PATENT DOCUMENTS

| 5,318,988 A | 6/1994 | Schohe-Loop et al. |
| 5,371,094 A | 12/1994 | Heine et al. |
| 5,741,789 A | 4/1998 | Hibschman et al. |
| 5,869,490 A | 2/1999 | Stack |
| 6,458,802 B1 | 10/2002 | Tran et al. |

FOREIGN PATENT DOCUMENTS

| WO | WO 91/13872 | 9/1991 |
| WO | WO 97/23485 | 7/1997 |
| WO | WO 98/29415 | 7/1998 |
| WO | WO 98/40386 | 9/1998 |

OTHER PUBLICATIONS

CA 130:168383, Gary P. Stack, 1999.
CA 128: 308493, Gary P. Stack, 1998.

Primary Examiner—Jane Fan
(74) Attorney, Agent, or Firm—Rebecca R. Barrett

(57) ABSTRACT

Compounds of the formula

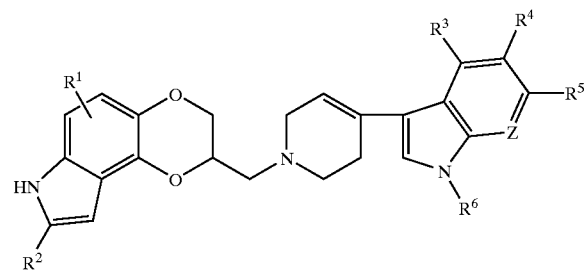

are useful in the treatment of central nervous system disorders including depression, obsessive compulsive disorder, panic attacks, generalized anxiety disorder, sexual dysfunction, eating disorders and addictive disorders caused by ethanol or cocaine abuse.

2 Claims, No Drawings

US 6,627,639 B2

USES FOR INDOLETETRAHYDROPYRIDINE DERIVATIVES OF 2,3-DIHYDRO-7H-[1,4] DIOXINO-[2,3-E]INDOLE

BACKGROUND OF THE INVENTION

This application is a continuation-in-part of co-pending application Ser. No. 10/131,339, filed on Apr. 24, 2002, which claims priority from provisional application serial No. 60/286,575, filed on Apr. 26, 2001, the entire disclosure of which is hereby incorporated by reference.

Major depression is a serious health problem affecting more than 5% of the population, with a life-time prevalence of 15–20%.

Selective serotonin reuptake inhibitors have produced significant success in treating depression and related illnesses and have become among the most prescribed drugs. They nonetheless have a slow onset of action, often taking several weeks to produce their full therapeutic effect. Furthermore, they are effective in fewer than two-thirds of patients.

Serotonin selective reuptake inhibitors (SSRIs) are well known for the treatment of depression and other conditions. SSRIs work by blocking the neuronal, reuptake of serotonin, thereby increasing the concentration of serotonin in the synaptic space, and thus increasing the activation of postsynaptic serotonin receptors.

However, although a single dose of an SSRI can inhibit the neuronal serotonin transporter which would be expected to increase synaptic serotonin, long-term treatment is required before clinical improvement is achieved.

It has been suggested that the SSRIs increase the serotonin levels in the vicinity of the serotonergic cell bodies and that the excess serotonin activates somatodendritic autoreceptors, 5-HT$_{1A}$ receptors, causing a decrease in serotonin release in major forebrain areas. This negative feedback limits the increment of synaptic serotonin that can be induced by antidepressants.

A 5-HT$_{1A}$ antagonist would limit the negative feedback and should improve the efficacy of the serotonin reuptake mechanism. (Perez, V., et al., *The Lancet*, 349:1594–1597 (1997)). Such a combination therapy would be expected to speed up the effect of the serotonin reuptake inhibitor.

Thus, it is highly desirable to provide improved compounds which both inhibit serotonin reuptake and which are antagonists of the 5-HT$_{1A}$ receptor.

DESCRIPTION OF THE INVENTION

In accordance with this invention, there is provided a group of novel compounds of the formula:

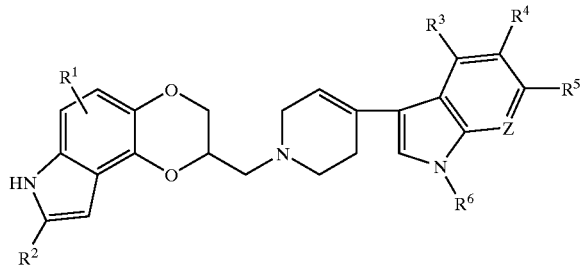

I wherein
$R^1$, $R^3$, $R^4$, $R^5$ and $R^7$ are, independently, hydrogen, halo, cyano, carboxamido, carboalkoxy of two to six carbon atoms, trifluoromethyl, alkyl of 1 to 6 carbon atoms, alkoxy of 1 to 6 carbon atoms, alkanoyloxy of 2 to 6 carbon atoms, amino, mono- or di-alkylamino in which each alkyl group has 1 to 6 carbon atoms, alkanamido of 2 to 6 carbon atoms, or alkanesulfonamido of 1 to 6 carbon atoms;
$R^2$ is hydrogen, halogen, alkyl of 1 to 6 carbon atoms or trifluoromethyl;
$R^6$ is hydrogen or alkyl of 1 to 6 carbon atoms;
Z is $CR^7$ or N;
and pharmaceutically acceptable salts thereof.

In some preferred embodiments of the invention $R^1$ is hydrogen, halo, cyano, trifluoromethyl, alkyl of 1 to 6 carbon atoms, or alkoxy of 1 to 6 carbon atoms. In still more preferred embodiments of the invention $R^1$ is hydrogen or alkyl of 1 to 6 carbon atoms. $R^1$ is still more preferably hydrogen.

In other embodiments of the invention $R^2$ is hydrogen, trifluoromethyl, or alkyl of one to six carbon atoms. In still more preferred embodiments of the present invention, $R^2$ is hydrogen or lower alkyl.

$R^3$, $R^4$ and $R^5$ are independently selected from hydrogen, halo, cyano, carboxamido, alkyl of 1 to 6 carbon atoms, and alkoxy of 1 to 6 carbon atoms in some embodiments of the invention. More preferably $R^3$, $R^4$ and $R^5$ are independently selected from halogen, cyano and hydrogen. Still more preferably, $R^3$, $R^4$ and $R^5$ are independently selected from halogen and hydrogen.

Where Z is $CR^7$, $R^7$ is preferably hydrogen, halo, cyano, carboxamido, alkyl of 1 to 6 carbon atoms, or alkoxy of 1 to 6 carbon atoms, more preferably $R^7$ is halogen, cyano or hydrogen. Still more preferably $R^7$ is halogen or hydrogen.

$R^6$ is preferably hydrogen or lower alkyl.

Most preferred are compounds where $R^1$ is hydrogen, halo, cyano, trifluoromethyl, alkyl of 1 to 6 carbon atoms or alkoxy of 1 to 6 carbon atoms, $R^2$ is hydrogen, trifluoromethyl or alkyl of 1 to 6 carbon atoms, $R^3$, $R^4$ and $R^5$ are independently selected from hydrogen, halo and cyano and $R^6$ is hydrogen.

Still more preferred compounds of the present invention are compounds where $R^1$ is hydrogen, $R^2$ is hydrogen or lower alkyl, $R^3$, $R^4$ and $R^5$ are independently selected from hydrogen and halogen, Z is $CR^7$, $R^6$ is hydrogen, and $R^7$ is hydrogen or halogen.

This invention relates to both the R and S stereoisomers of the 2,3-dihydro-7H-[1,4]dioxino[2,3-e]indole derivatives as well as to mixtures of the R and S stereoisomers. Throughout this application, the name of the product of this invention, where the absolute configuration of the 2,3-dihydro-7H-[1,4]dioxino[2,3-e]indole derivative is not indicated, is intended to embrace the individual R and S enantiomers as well as mixtures of the two. In some preferred embodiments of the present invention the S stereoisomer is preferred.

Where a stereoisomer is preferred, it may in some embodiments, be provided substantially free of the corresponding enantiomer. Thus, an enantiomer substantially free of the corresponding enantiomer refers to a compound which is isolated or separated via separation techniques or prepared free of the corresponding enantiomer. Substantially free, as used herein means that the compound is made up of a significantly greater proportion of one stereoisomer. In preferred embodiments the compound is made up of at least about 90% by weight of a preferred stereoisomer. In other embodiments of the invention, the compound is made up of at least about 99% by weight of a preferred stereoisomer. Preferred stereoisomers may be isolated from racemic mixtures by any method known to those skilled in the art, including high performance liquid chromatography (HPLC) and the formation and crystallization of chiral salts or by methods described herein. See, for example, Jacques, et al., *Enantiomers, Racemates and Resolutions* (Wiley Interscience, New York, 1981); Wilen, S. H., et al., *Tetrahedron* 33:2725 (1977); Eliel, E. L. *Stereochemistry of Carbon Compounds* (McGraw-Hill, NY, 1962); Wilen, S. H. *Tables of Resolving Agents and Optical Resolutions* p. 268 (E. L. Eliel, Ed., Univ. of Notre Dame Press, Notre Dame, Ind. 1972).

Alkyl as used herein refers to an aliphatic hydrocarbon chain and includes straight and branched chains such as methyl, ethyl, n-propyl, isopropyl, n-butyl, isobutyl, sec-butyl, t-butyl, n-pentyl, isopentyl, neo-pentyl, n-hexyl, and isohexyl. Lower alkyl refers to alkyl having 1 to 3 carbon atoms.

Alkanamido as used herein refers to the group R—C(=O)—NH— where R is an alkyl group of 1 to 5 carbon atoms.

Alkanoyloxy as used herein refers to the group R—C(=O)—O— where R is an alkyl group of 1 to 5 carbon atoms.

Alkanesulfonamido as used herein refers to the group R—S(O)$_2$—NH— where R is an alkyl group of 1 to 6 carbon atoms.

Alkoxy as used herein refers to the group R—O— where R is an alkyl group of 1 to 6 carbon atoms.

Carboxamido as used herein refers to the group —CO—NH$_2$.

Carboalkoxy as used herein refers to the group R—O—C(=O)— where R is an alkyl group of 1 to 5 carbon atoms.

Halogen (or halo) as used herein refers to chlorine, bromine, fluorine and iodine.

Pharmaceutically acceptable salts are those derived from such organic and inorganic acids as: acetic, lactic, citric, cinnamic, tartaric, succinic, fumaric, maleic, malonic, mandelic, malic, oxalic, propionic, hydrochloric, hydrobromic, phosphoric, nitric, sulfuric, glycolic, pyruvic, methanesulfonic,iethanesulfonic, toluenesulfonic, salicylic, benzoic, and similarly known acceptable acids.

Specific examples of the present invention include:

2-[(4-(1H-Indol-3-yl)-3,6-dihydropyridin-1(2H)-yl)methyl]-8-methyl-2,3-dihydro-7H-[1,4]dioxino[2,3-e]indole;

2-[(4-(1H-Indol-3-yl)-3,6-dihydropyridin-1(2H)-yl)methyl]-2,3-dihydro-7H-[1,4]dioxino[2,3-e]indole;

2-{[4-(5-Fluoro-1H-indol-3-yl)-3,6-dihydropyridin-1(2H)-yl]methyl}-2,3-dihydro-7H-[1,4]dioxino[2,3-e]indole;

8-ethyl-2-[(4-(1H-indol-3-yl)-3,6-dihydropyridin-1(2H)nyl)methyl]-2,3-dihydro-7H-[1,4]dioxino[2,7-e]indole; and 8-ethyl-2-[(4-(5-fluoro-1H-indol-3-yl)3,6-dihydropyridin-1(2H)-yl)methyl]-2,3-dihydro-7H-[1,4]dioxino[2,7-e]indole.

The 2,3-dihydro-7H-[1,4]dioxino[2,3-e]indoles of Formula I are prepared as illustrated below. Specifically, the appropriately substituted nitroguaiacol (1) is alkylated with allyl bromide in the presence of a suitable base such as sodium hydride to produce (2) and then demethylated by a reagent such as sodium hydroxide. The resulting 4-nitro-2-allyloxyphenol (3) is then alkylated with glycidyl tosylate or an epihalohydrin in the presence of a base such as sodium hydride to produce (4) and heated in a high boiling solvent such as mesitylene or xylene to effect both Claisen rearrangement of the allyl group and cyclization of the dioxan ring. The resulting primary alcohol (5) is converted to the tosylate (6) by reaction with p-toluenesulfonyl chloride in the presence of a tertiary amine or pyridine, or alternatively to a halide by reaction with carbon tetrabromide or carbon tetrachloride in combination with triphenylphosphine. The allyl side chain is then cleaved to the aldehyde (7) by treatment with ozone at low temperature, followed by work-up with a tertiary base such as diisopropylethylamine or triethylamine, or by treatment with catalytic osmium tetroxide and sodium periodate. Reduction of the nitro group with hydrogen over platinum oxide leads directly to formation of the indole (8) in which R$^2$ is hydrogen. Alternatively, the aldehyde may be treated with an appropriate alkyl Grignard reagent or with trifluoromethyl trimethylsilane in the presence of cesium fluoride, then oxidized

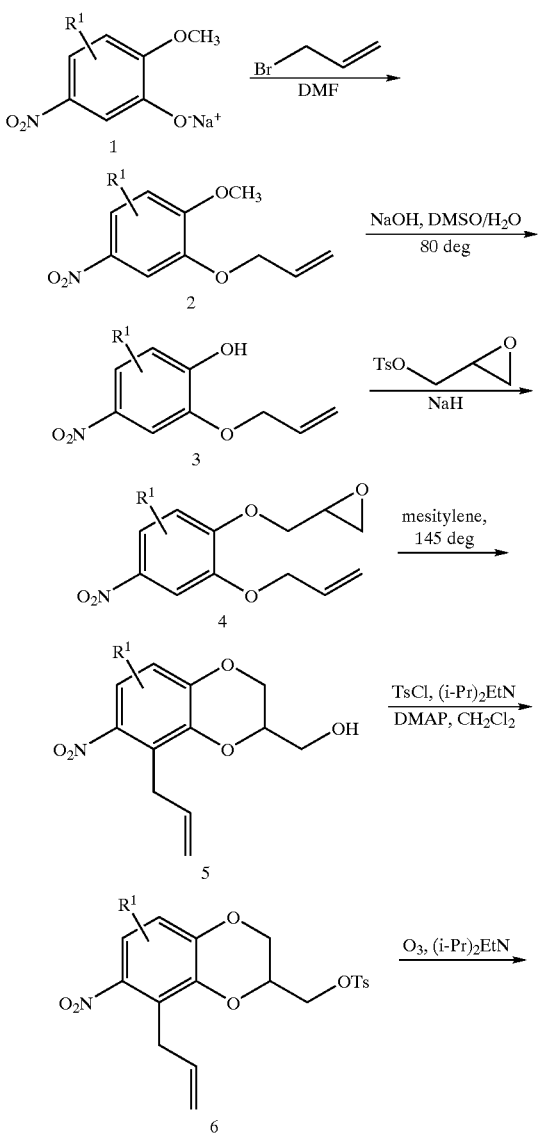

Scheme I

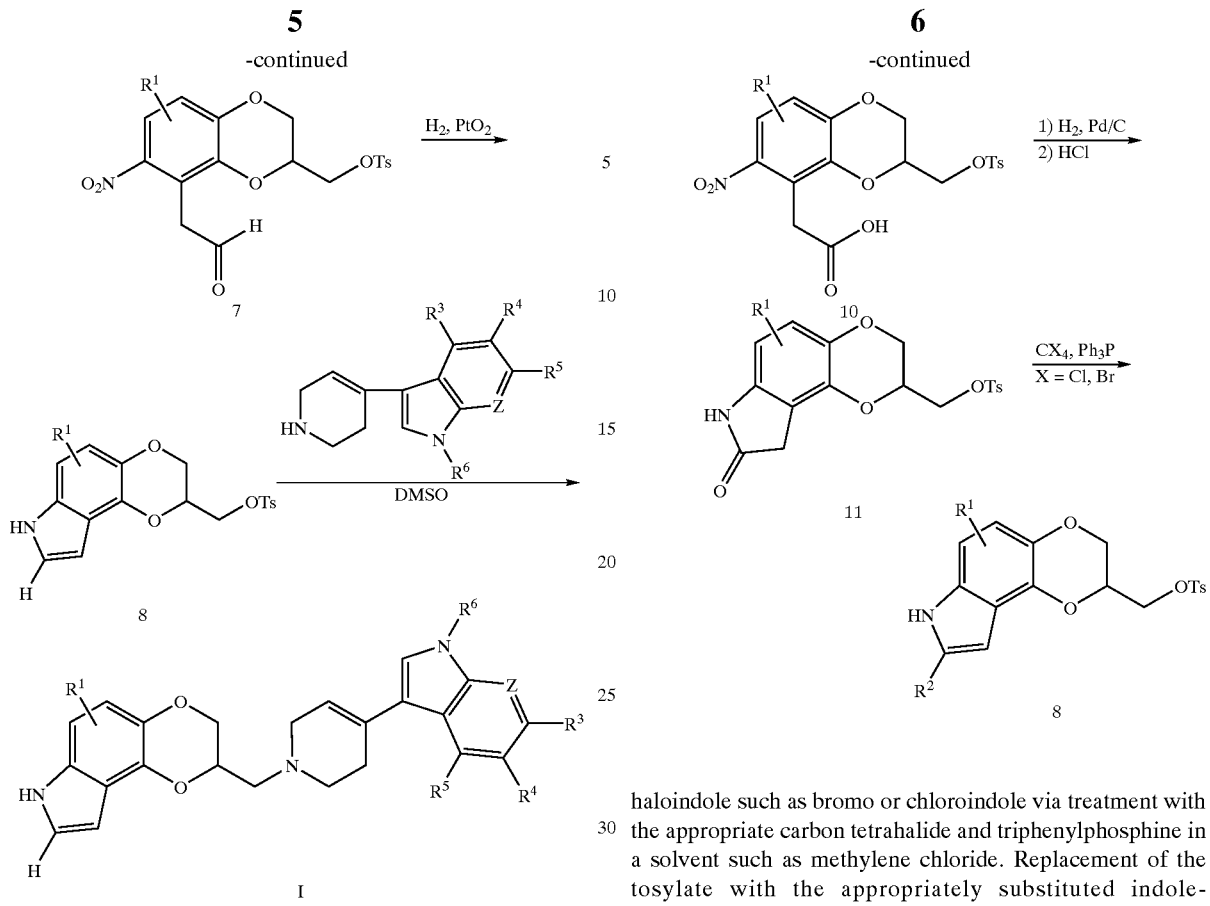

to a ketone with a suitable oxidant such as pyridinium chlorochromate (PCC) or the Swern reagent and reduced with hydrogen over platinum oxide to give the indoles in which R² is alkyl or trifluoromethyl. Replacement of the tosylate or halide with the appropriately substituted indole-tetrahydropyridine in some high boiling solvent such as dimethyl sulfoxide gives the title compounds of the invention.

The compounds of the invention in which R² is a halogen such as chlorine or bromine are prepared from the nitroaldehyde (7) described above by the procedure of Scheme II. The aldehyde is oxidized to the phenylacetic acid (10) by a suitable oxidant such as the Jones reagent (CrO₃, H₂SO₄ in acetone) and then the nitro group is reduced to the amine (11) by treatment with hydrogen in the presence of a catalyst such as palladium on carbon. Cyclization to the oxindole is effected by treatment with acid and the oxindole converted to the haloindole such as bromo or chloroindole via treatment with the appropriate carbon tetrahalide and triphenylphosphine in a solvent such as methylene chloride. Replacement of the tosylate with the appropriately substituted indole-tetrahydropyridine in some high boiling solvent such as dimethyl sulfoxide gives the title compounds of the invention.

The compounds of the invention may alternatively be prepared from the 7-nitro-8-allyl benzodioxan derived from the Claisen rearrangement by the procedure of Scheme III. The alcohol is converted to the tosylate or halide (6) as described above and the double bond is isomerized by treatment with bis-acetonitrile palladium (II) chloride in refluxing methylene chloride or benzene. Cleavage of the olefin with ozone or osmium tetroxide/periodate gives the o-nitrobenzaldehyde (12), which is condensed with the appropriate nitroalkane in the presence of a suitable base catalyst to yield the corresponding o,β-dinitrostyrene (13). Reduction of both nitro groups with hydrogen over palladium on carbon is accompanied by cyclization to form the indole (8). Replacement of the tosylate with the appropriately substituted indoletetrahydropyridine as above gives the title compounds of the invention.

Scheme II

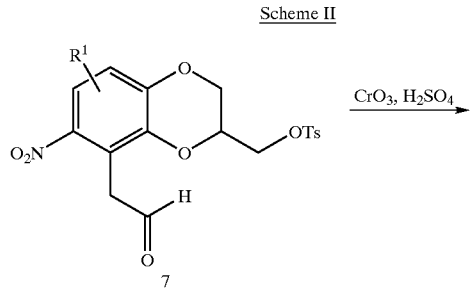

Scheme III

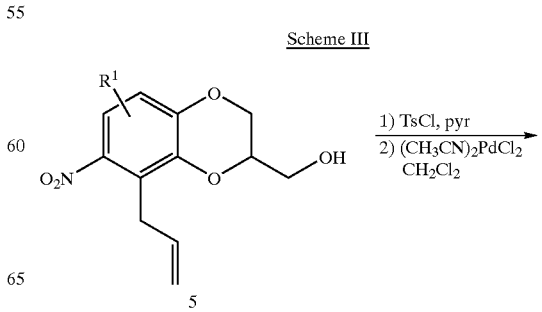

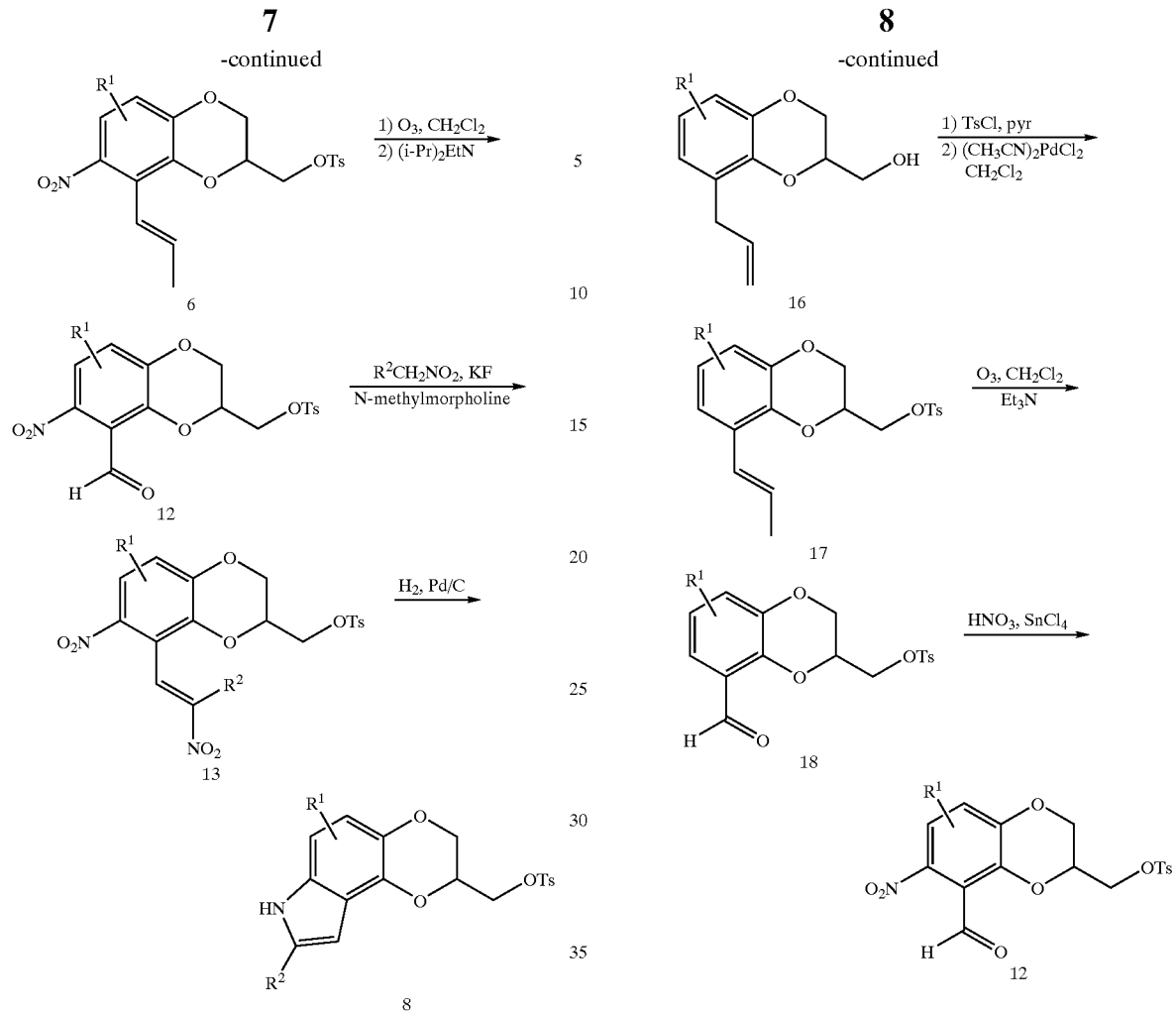

sodium periodate as described above, the resulting aldehyde (18) is regioselectively nitrated with a combination of nitric acid and tin (IV) chloride to produce (12).

Compounds of the invention in which $R^2$ is methyl may be most conveniently prepared from the 7-nitro-8-allyl benzodioxan (6) described above by the procedure of Scheme V. The nitro group is The o-nitrobenzaldehyde used in the condensation described above may be alternatively prepared as shown in Scheme IV. The appropriate mono-allylated catechol (14) is elaborated with glycidyl tosylate as described above (15) and rearranged in refluxing mesitylene. Cyclization to the benzodioxan methanol (16) is effected by treatment with sodium bicarbonate in ethanol and the alcohol is converted to the tosylate or halide (17) as described above. After rearrangement of the double bond by treatment with catalytic bis-acetonitrile palladium (II) chloride in refluxing methylene chloride and cleavage with ozone or osmium tetroxide and Scheme IV

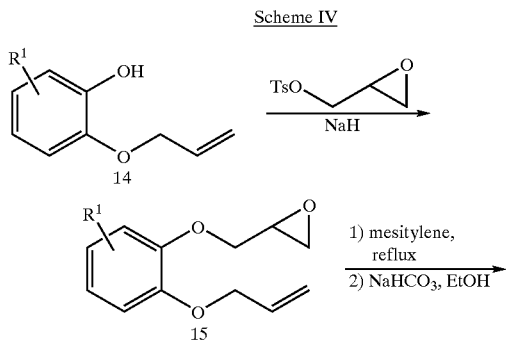

Scheme V

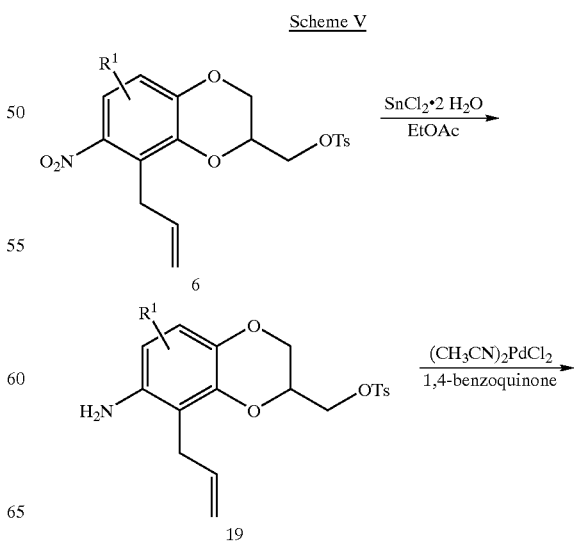

-continued

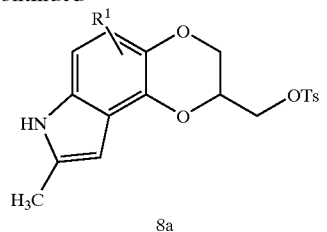
8a reduced with tin (II) chloride dihydrate in refluxing ethyl acetate to produce (19) and cyclization to the 2-methylindole (8a) effected by several days' treatment with catalytic bis-acetonitrile (II) chloride, lithium chloride and 1,4-benzoquinone at room temperature in tetrahydrofuran. Replacement of the tosylate with the appropriately substituted indoletetrahydropyridine as above gives the title compounds of the invention The guaiacols, catechols and indoletetrahydropyridines appropriate to the above chemistry are known compounds or can be prepared by one schooled in the art. The compounds of the invention may be resolved into their enantiomers by conventional methods or, preferably, the individual enantiomers may be prepared directly by substitution of (2R)-(−)-glycidyl 3-nitrobenzenesulfonate or tosylate (for the S benzodioxan methanamine) or (2S)-(+)-glycidyl 3-nitrobenzenesulfonate or tosylate (for the R enantiomer) in place of epihalohydrin or racemic glycidyl tosylate in the procedures above.

A protocol similar to that used by Cheetham et. al. (Neuropharmacol. 32:737, 1993) was used to determine the affinity of the compounds of the invention for the serotonin transporter. The compound's ability to displace $^3$H-paroxetine from male rat frontal cortical membranes was determined using a Tom Tech filtration device to separate bound from free $^3$H-paroxetine and a Wallac 1205 Beta Plate® counter to quantitate bound radioactivity. $K_i$'s thus determined for standard clinical antidepressants are 1.96 nM for fluoxetine, 14.2 nM for imipramine and 67.6 nM for zimelidine. A strong correlation has been found between $^3$H-paroxetine binding in rat frontal cortex and $^3$H-serotonin uptake inhibition.

High affinity for the serotonin 5-HT$_{1A}$ receptor was established by testing the claimed compound's ability to displace [$^3$H] 8-OHDPAT (dipropylaminbtetralin) from the 5-HT$_{1A}$ serotonin receptor following a modification of the procedure of Hall et al., J. Neurochem. 44, 1685 (1985) which utilizes CHO cells stably transfected with human 5-HT$_{1A}$ receptors. The 5-HT$_{1A}$ affinities for the compounds of the invention are reported below as $K_i$'s.

Antagonist activity at 5-HT$_{1A}$ receptors was established by using a $^{35}$S-GTPγS binding assay similar to that used by Lazareno and Birdsall (Br. J. Pharmacol. 109: 1120, 1993), in which the test compound's ability to affect the binding of $^{35}$S-GTPγS to membranes containing cloned human 5-HT$_{1A}$ receptors was determined. Agonists produce an increase in binding whereas antagonists produce no increase but rather reverse the effects of the standard agonist 8-OHDPAT. The test compound's maximum inhibitory effect is represented as the $I_{max}$, while its potency is defined by the IC$_{50}$.

The results of the three standard experimental test procedures described in the preceding three paragraphs were as follows:

| Compound | 5-HT Transporter Affinity KI (nM) | 5-HT$_{1A}$ Receptor Affinity KI (nM) | 5-HT$_{1A}$ Function IC$_{50}$ (nM) (I$_{max}$) |
|---|---|---|---|
| Example 1 | 3.44 | 0.45 | 16.0 (100) |
| Example 2 | 0.77 | 1.55 | 23.0 (52) |
| Example 3 | 1.23 | 2.45 | 11.3 (100) |
| Example 4 | 10.00 | 4.56 | 73.0 (78) |
| Example 5 | 10.00 | 26.34 | 265.5 (98) |

Like the antidepressants fluoxetine, paroxetine and sertraline, the compounds of this invention have the ability to potently block the reuptake of the brain neurotransmitter serotonin. They are thus useful for the treatment of depression and other diseases commonly treated by the administration of serotonin selective reuptake inhibitor (SSRI) antidepressants. Moreover, the compounds of this invention have potent affinity for and antagonist activity at brain 5-HT$_{1A}$ serotonin receptors. Recent clinical trials employing drug mixtures (eg, fluoxetine and pindolol) have demonstrated a more rapid onset of antidepressant efficacy for a treatment combining SSRI activity and 5-HT$_{1A}$ antagonism (Blier and Bergeron, 1995; F. Artigas et. al., 1996; M. B. Tome et. al., 1997). The compounds of the invention are thus exceedingly interesting and useful for treating depressive illnesses.

Hence, the compounds of this invention are combined serotonin reuptake inhibitors/5-HT$_{1A}$ antagonists and are useful for the treatment of conditions related to or affected by the reuptake of serotonin and by the serotonin 1A receptor, such as depression (including but not limited to major depressive disorder, childhood depression and dysthymia), anxiety, panic disorder, post-traumatic stress disorder, premenstrual dysphoric disorder (also known as pre-menstrual syndrome), attention deficit disorder (with and without hyperactivity), obsessive compulsive disorder (including trichotillomania), social anxiety disorder, generalized anxiety disorder, obesity, eating disorders such as anorexia nervosa, bulimia nervosa, vasomotor flushing, cocaine and alcohol addiction, sexual dysfunction (including premature ejaculation), and related illnesses.

Thus the present invention provides methods of treating, preventing, inhibiting or alleviating each of the maladies listed above in a mammal, preferably in a human, the methods comprising providing a pharmaceutically effective amount of a compound of this invention to the mammal in need thereof.

Also encompassed by the present invention are pharmaceutical compositions for treating or controlling disease states or conditions of the central nervous system comprising at least one compound of Formula I, mixtures thereof, and or pharmaceutical salts thereof, and a pharmaceutically acceptable carrier therefore. Such compositions are prepared in accordance with acceptable pharmaceutical procedures, such as described in Remingtons Pharmaceutical Sciences, 17th edition, ed. Alfonoso R. Gennaro, Mack Publishing Company, Easton, Pa. (1985). Pharmaceutically acceptable carriers are those that are compatible with the other ingredients in the formulation and biologically acceptable.

The compounds of this invention may be administered orally or parenterally, neat or in combination with conventional pharmaceutical carriers. Applicable solid carriers can include one or more substances which may also act as flavoring agents, lubricants, solubilizers, suspending agents, fillers, glidants, compression aids, binders or tablet-disintegrating agents or an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers may be used in preparing solutions, suspensions, emulsions, syrups and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above e.g. cellulose derivatives, preferably sodium carboxymethyl cellulose solution), alcohols (including monohydric alcohols and polyhydric alcohols e.g. glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection. Sterile solutions can also be administered intravenously. Oral administration may be either liquid or solid composition form.

Preferably the pharmaceutical composition is in unit dosage form, e.g. as tablets, capsules, powders, solutions, suspensions, emulsions, granules, or suppositories. In such form, the composition is sub-divided in unit dose containing appropriate quantities of the active ingredient; the unit dosage forms can be packaged compositions, for example, packeted powders, vials, ampoules, prefilled syringes or sachets containing liquids. The unit dosage form can be, for example, a capsule or tablet itself, or it can be the appropriate number of any such compositions in package form.

The amount provided to a patient will vary depending upon what is being administered, the purpose of the administration, such as prophylaxis or therapy, and the state of the patient, the manner of administration, and the like. In therapeutic applications, compounds of the present invention are provided to a patient already suffering from a disease in an amount sufficient to cure or at least partially ameliorate the symptoms of the disease and its complications. An amount adequate to accomplish this is defined as a "therapeutically effective amount." The dosage to be used in the treatment of a specific case must be subjectively determined by the attending physician. The variables involved include the specific condition and the size, age and response pattern of the patient. Generally, a starting dose is about 5 mg per day with gradual increase in the daily dose to about 150 mg per day, to provide the desired dosage level in the human.

Provide, as used herein, means either directly administering a compound or composition of the present invention, or administering a prodrug, derivative or analog which will form an equivalent amount of the active compound or substance within the body.

The present invention includes prodrugs of compounds of Formula I. "Prodrug", as used herein means a compound which is convertible in vivo by metabolic means (e.g. by hydrolysis) to a compound of Formula I. Various forms of prodrugs are known in the art, for example, as discussed in Bundgaard, (ed.), Design of Prodrugs, Elsevier (1985); Widder, et al. (ed.), Methods in Enzymology, vol. 4, Academic Press (1985); Krogsgaard-Larsen, et al., (ed). "Design and Application of Prodrugs, Textbook of Drug Design and Development, Chapter 5, 113–191 (1991), Bundgaard, et al., Journal of Drug Deliver Reviews, 8:1–38(1992), Bundgaard, J. of Pharmaceutical Sciences, 77:285 et seq. (1988); and Higuchi and Stella (eds.) Prodrugs as Novel Drug Delivery Systems, American Chemical Society (1975).

The following examples illustrate the production of representative compounds of this invention.

INTERMEDIATE 1

3-Allyloxy-4-methoxynitrobenzene 97.5 g (0.51 mole) of the sodium salt of 5-nitroguaiacol was dissolved in one liter of N,N-dimethylformamide and 1.5 equivalents of allyl bromide added. The reaction was heated to 65° C. for two hours, after which time much of the dark color had discharged and tlc (1:1 methylene chloride/hexane) indicated loss of starting material. The solvent was concentrated in vacuum and the residue washed with water. The product was isolated by filtration and dried in a vacuum. This gave, 112 g of pale yellow solid. A sample recrystallized from methanol gave m.p. 93–94° C.

INTERMEDIATE 2

2-Allyloxy-4-nitrophenol

To one liter of dimethyl sulfoxide was added 750 mL of 2 N aqueous sodium hydroxide and the mixture was heated to 65° C. The pale yellow solid 3-allyloxy-4-methoxynitrobenzene prepared above was added in portions over a 30 minute period and then the temperature was raised to 95° C. and maintained for 3 hours, after which time the starting material had been consumed. The mixture was allowed to cool and poured into a mixture of 1 L ice and 1 L 2 N HCl. 73 Grams of crude but homogeneous (by tlc 1:1 methylene chloride/hexane) desired product was isolated as a light brown solid by filtration. This material was subsequently dissolved in 1:1 hexane/methylene chloride and filtered through silica gel to give 68 g of pale yellow solid, which, when recrystallized from ethyl/acetate/hexane, gave m.p. 61–62° C. The aqueous mother liquors from the initial crystallization above were extracted with 2 L of ethyl acetate. This was dried over sodium sulfate, filtered and evaporated to a dark oil. Column chromatography on silica with 1:1 methylene chloride/hexane gave an additional 12 g of the title compound as a yellow solid. Elution with 2% methanol in chloroform gave 12 g of a dark oil which slowly crystallized in vacuum. This proved to be the Claisen product, 3-allyl-4-nitrocatechol.

INTERMEDIATE 3

2-(2-Allyloxy-4-nitrophenoxymethyl)-oxirane 20 g (0.50 mole) of 60% NaH/mineral oil was placed in a two liter flask and washed with 500 mL of hexane. 1 L of N,N-dimethylformamide was added, followed by 77 g (0.40 mole) of the 2-allyloxy-4-nitrophenol prepared in the previous step. Addition of the phenol was performed in portions under argon. After stirring the mixture for 30 minutes at room temperature under argon, 108 g (0.48 moles) of (R)-glycidyl tosylate was added and the mixture heated at 70–75° C. under nitrogen overnight. Upon cooling, the solvent was removed in vacuum and replaced with one liter of methylene chloride. This was washed with 500 mL portions of 2 N HCl (aq), saturated aqueous sodium bicarbonate and saturated brine and dried over sodium sulfate. The mixture was filtered, concentrated to an oil in vacuum and column chromatographed on silica gel using 1:1 hexane/methylene chloride as eluant. This gave 43 g of product contaminated with traces of the two starting materials, followed by 21 g of pure product as a pale yellow solid. The impure material was recrystallized from 1.2 L of 10% ethyl acetate/hexane to give 34 g of pure (homogeneous on silica gel tlc with 1:1 hexane/methylene chloride) (R)-2-(2-allyloxy-4-nitrophenoxymethyl)-oxirane (m.p. 64° C.).

Elemental Analysis for: $C_{12}H_{13}NO_5$; Calc'd: C, 57.37; H, 5.21; N, 5.58. Found: C, 57.50; H, 5.21; N, 5.43.

INTERMEDIATE 4

(8-Allyl-7-nitro-2,3-dihydro-benzo(1,4)dioxin-2-yl)-methanol (R)-2-(2-Allyloxy-4-nitrophenoxymethyl)-oxirane (20 g, 80 mmoles) prepared as above was heated at 155° C. in mesitylene for 24 hours under nitrogen. Filtration of the black solid which formed gave 1.5 g of very polar material. Evaporation of the solvent in vacuum followed by column chromatography on silica gel with methylene chloride as eluant gave 10 g of recovered starting material and 7.5 g of the desired rearranged (S)-(8-allyl-7-nitro-2,3-dihydro-benzo(1,4)dioxin-2-yl)-methanol, which slowly crystallized on standing in vacuum (m.p. 67° C.). The yield based on recovered starting material is 75%.

Elemental Analysis for: $C_{12}H_{13}NO_5$. Calc'd: C, 57.37; H, 5.21; N, 5.58. Found: C, 57.26; H, 5.20; N, 5.35.

INTERMEDIATE 5

Toluene-4-sulfonic Acid 8-Allyl-7-nitro-2,3-dihydro-benzo(1,4)dioxin-2-ylmethyl Ester 9.55 g (38.0 mmole) of (S)-(8-allyl-7-nitro-2,3-dihydro-benzo(1,4)dioxin-2-yl)-methanol was dissolved in 465 mL of pyridine, 29.0 g (152 mmole) of p-toluenesulfonyl chloride was added and the mixture stirred at room temperature under nitrogen overnight. Water was then added to quench the excess tosyl chloride and the solvent was removed in vacuum and replaced with methylene chloride. This solution was washed with 2 N HCl (aq), with saturated aqueous sodium bicarbonate, and with saturated brine, and dried over magnesium sulfate. Filtration, evaporation in vacuum and column chromatography on silica gel with 1:1 hexane/methylene chloride as eluant gave 12.6 g (92%) of toluene-4-sulfonic acid (R)-allyl-7-nitro-2,3-benzo(1,4)dioxin-2-ylmethyl ester, which slowly crystallized to a tan solid (m.p. 60–62° C.) upon standing.

Elemental Analysis for: $C_{19}H_{19}NO_7S$; Calc'd: C, 56.29; H, 4.72; N, 3.45. Found: C, 56.13; H, 4.58; N, 3.44.

INTERMEDIATE 6

[8-Allyl-7-amino-2,3-dihydro-1,4-benzodioxin-2-yl]methyl 4-Methylbenzenesulfonate (2R)-Toluene-4-sulfonic acid 8-allyl-7-nitro-2,3-dihydro-benzo(1,4)dioxin-2-ylmethyl ester (5.3 g, 13 mmole) and tin (II) chloride dihydrate (14.7 g, 65 mmole) were combined in 500 mL of ethyl acetate and the mixture refluxed for 3 hours under nitrogen. The reaction was allowed to cool to room temperature and was quenched by the addition of 300 mL of saturated aqueous sodium bicarbonate. The biphasic mixture was filtered through celite, the phases separated and the aqueous back-extracted with 200 mL of ethyl acetate. The combined organic phases were washed with 250 mL portions of water and saturated brine, dried over sodium sulfate, filtered and concentrated in vacuum. The residue was column chromatographed on silica gel with methylene chloride as eluant to give 2.2 g of the (R)-enantiomer of the title compound as an orange oil. $^1$H-NMR (CDCl$_3$): doublet 7.8 δ (2H); doublet 7.35 δ (2H); doublet 6.6 δ (1H); doublet 6.25 δ (1H); multiplet 5.8 δ (1H); singlet 5.05 δ (1H); doublet 5.0 δ (1H); multiplet 4.4 δ (1H); multiplet 4.2 δ (3H); doublet of doublets 4.0 δ (1H); doublet 3.25 δ (2H); singlet 2.45 δ (3H).

INTERMEDIATE 7

[8-Methyl-2,3-dihydro-7H-[1,4]dioxino[2,3-e]indol-2-yl]methyl 4-Methylbenzenesulfonate Bis-acetonitrile (II) chloride (0.153 g, 0.60 mmole), 1,4-benzoquinone (0.64 g, 6.0 mmole) and lithium chloride (2.5 g, 60 mmole) were combined in 85 mL of tetrahydrofuran and the mixture stirred under argon for 5 minutes. A solution of (2R)-[8-allyl-7-amino-2,3-dihydro-1,4-benzodioxin-2-yl]methyl 4-methylbenzene-sulfonate (2.2 g, 5.9 mmole) in 25 mL of tetrahydrofuran was added and the mixture stirred for 48 hours at room temperature. The mixture was then diluted with 300 mL of ethyl acetate and washed with 200 mL portions of 1 N aqueous HCl, saturated aqueous sodium bicarbonate and brine, dried over magnesium sulfate, filtered and concentrated in vacuum. Column chromatography on silica gel with methylene chloride as eluant gave 1.1 g of the (R)-enantiomer of the title compound as a gray foam. $^1$H-NMR (CDCl$_3$): doublet 7.8 δ (2H); broad singlet 7.75 δ (1H); doublet 7.3 δ (2H); doublet 6.75 δ (1H); doublet 6.63 δ (1H); singlet 6.1 δ (1H); multiplet 4.5 δ (1H); multiplet 4.25 δ (3H); doublet of doublets 4.07 δ (1H); singlet 2.43 δ (3H); singlet 2.40 δ (3H).

EXAMPLE 1

2-[(4-(1H-Indol-3-yl)-3,6-dihydropyridin-1(2H)-yl)methyl]-8-methyl-2,3-dihydro-7H-[1,4]dioxino[2,3-e]indole A solution of 0.55 g (1.5 mmole) of [(2R)-8-methyl-2,3-dihydro-7H-[1,4]dioxino[2,3-e]indol-2-yl]methyl 4-methylbenzenesulfonate and 0.50 g (2.5 mmole) of 3-(1,2,3,6-tetrahydro-4-pyridinyl)-1H-indole in 6.0 mL of DMSO was heated at 65–7° C. for 4 hours. The mixture was diluted with 300 mL of ethyl acetate, washed with 200 ml portions of saturated aqueous sodium bicarbonate and saturated brine, dried over magnesium sulfate, filtered and concentrated in vacuum. The residue was column chromatographed on silica gel with 1% methanol in chloroform as eluant to give 0.21 g of the (S)-enantiomer of the title compound as a yellow solid, m.p. 212–215° C.

Elemental Analysis for: $C_{25}H_{25}N_3O_2 \cdot 0.50H_2O$; Calc'd: C, 73.51; H, 6.42; N, 10.29. Found: C, 73.64; H, 6.31; N, 10.28.

INTERMEDIATE 8

[7-Nitro-8-(2-oxoethyl)-2,3-dihydro-1,4-benzodioxin-2-yl]methyl 4-Methylbenzenesulfonate A solution of 4.2 g (10 mmole) of toluene-4-sulfonic acid (2R)-8-allyl-7-nitro-2,3-dihydro-benzo(1,4)dioxin-2- ylmethyl ester in 400 mL of methylene chloride was cooled in a dry ice/isopropanol bath and saturated with ozone. It was then purged with oxygen and 2.6 g (20 mmole) of diisopropylethylamine added. The mixture was allowed to come to room temperature and stirred under nitrogen for 24 hours. It was then washed with 300 mL portions of 2 N HCl (aq), water and saturated brine, dried over magnesium sulfate, filtered and concentrated in vacuum to give 3.8 g of the (R)-enantiomer of the title compound as a white solid one-quarter hydrate, m.p. 116–120° C.

Elemental Analysis for: $C_{18}H_{17}NO_8S.0.25H_2O$; Calc'd: C, 52.49; H, 4.28; N, 3.40. Found: C, 52.33; H, 3.92; N, 3.36.

INTERMEDIATE 9

2,3-Dihydro-7H-[1,4]dioxino[2,3-e]indol-2-ylmethyl 4-Methylbenzenesulfonate

A mixture of 3.75 g (9.2 mmole) of [(2R)-7-nitro-8-(2-oxoethyl)-2,3-dihydro-1,4-benzodioxin-2-yl]methyl 4-methylbenzenesulfonate and 3.0 g of platinum oxide in 50 mL of ethyl acetate was treated with 45 psi of hydrogen on a Parr hydrogenation apparatus for 6 hours. The mixture was then filtered through celite and concentrated in vacuum. The residue was column chromatographed on silica gel with first 10% hexane/methylene chloride, then 1% methanol/methylene chloride and finally 2% methanol/methylene chloride to give 1.50 g of the (R)-enantiomer of the title compound as a white solid one-quarter hydrate, m.p. 145° C.

Elemental Analysis for: $C_{18}H_{17}NO_5S.0.25H_2O$; Calc'd: C, 59.41; H, 4.85; N, 3.85. Found: C, 59.41; H, 4.57; N, 3.72.

EXAMPLE 2

2-[(4-(1H-Indol-3-yl)-3,6-dihydropyridin-1(2H)-yl) methyl]-2,3-dihydro-7H-[1,4]dioxino[2,3-e]indole A solution of 0.65 g (1.8 mmole) of (2R)-2,3-dihydro-7H-[1,4]dioxino[2,3-e]indol-2-ylmethyl 4-methylbenzenesulfonate and 0.71 g (3.6 mmole) of 3-(1,2,3,6-tetrahydro-4-pyridinyl)-1H-indole in 30 mL of DMSO was heated at 65° C. for 4 hours. The mixture was diluted with 300 mL of ethyl acetate, washed with 200 ml portions of saturated aqueous sodium bicarbonate and saturated brine, dried over magnesium sulfate, filtered and concentrated in vacuum. The residue was column chromatographed on silica gel with 2–4% methanol in methylene chloride as eluant. The product fractions were combined and concentrated in vacuum, and the residue triturated with methylene chloride/hexane (1:1) to give 0.39 g of the (S)-enantiomer of the title compound as a yellow solid, m.p. 126° C., which retains one equivalent of DMSO.

Elemental Analysis for: $C_{24}H_{23}N_3O_2.0.25H_2O.C_2H_6OS$; Calc'd: C, 66.71; H, 6.35; N, 8.98. Found: C, 66.85; H, 6.18; N, 8.77.

EXAMPLE 3

2-{[4-(5-Fluoro-1H-indol-3-yl)-3,6-dihydropyridin-1 (2H)-yl]methyl}-2,3-dihydro-7H-[1,4]dioxino[2,3-e] indole A solution of 0.30 g (0.84 mmole) of (2R)-2,3-dihydro-7H-[1,4]dioxino[2,3-e]indol-2-ylmethyl 4-methylbenzenesulfonate and 0.40 g (1.8 mmole) of 5-fluoro-3-(1,2,3,6-tetrahydro-4-pyridinyl)-1H-indole in 30 mL of DMSO was heated at 65° C. for 4 hours. The mixture was diluted with 300 mL of ethyl acetate, washed with 200 ml portions of saturated aqueous sodium bicarbonate and saturated brine, dried over magnesium sulfate, filtered and concentrated in vacuum. The residue was column chromatographed on silica gel with 0–1.5% methanol in methylene chloride as eluant. The product fractions were combined and concentrated in vacuum, and the residue triturated with ether/hexane (1:1) to give 0.10 g of the (S)-enantiomer of the title compound as a yellow solid, m.p. 112° C., with one-quarter mole of ether.

Elemental Analysis for: $C_{24}H_{22}FN_3O_2.0.25C_4H_{10}O$; Calc'd: C, 71.16; H, 5.85; N, 9.96. Found: C, 71.10; H, 5.42; N, 9.77.

INTERMEDIATE 10

{7-Nitro-8-[1-propenyl]-2,3-dihydro-1,4-benzodioxin-2-yl}methyl 4-Methylbenzenesulfonate To a solution of 10.0 g (24.0 mmole) of (R)-[8-allyl-7-nitro-2,3-dihydro-1,4-benzodioxin-2-yl]methyl 4-methylbenzenesulfonate in 700 mL of benzene was added 1.03 g of bis(acetonitrile)dichloropalladium (II) and the mixture was refluxed under nitrogen for 48 hours. The catalyst was then removed by filtration and the filtrate concentrated in vacuum to a brown oil. Column chromatography on silica gel with methylene chloride as eluant gave 7.2 g of the title compound as a mixture of E and Z isomers. A sample of {(2R)-7-nitro-8[(E)-1-propenyl]-2,3-dihydro-1,4-benzodioxin-2-yl}methyl 4-methylbenzenesulfonate was obtained as a yellow solid (m.p. 105–106° C.) by evaporation of a pure E isomer-containing fraction.

Elemental Analysis for: $C_{19}H_{19}NO_7S$ Calc'd: C, 56.29; H, 4.72; N, 3.45. Found: C, 56.12; H, 4.64; N, 3.39.

INTERMEDIATE 11

(8-Formyl-7-nitro-2,3-dihydro-1,4-benzodioxin-2-yl) methyl 4-Methylbenzenesulfonate {(2R)-7-Nitro-8-[1-propenyl]-2,3-dihydro-1,4-benzodioxin-2-yl}methyl 4-methylbenzenesulfonate (10.5 g, 25.9 mmole) dissolved in 400 mL of methylene chloride was treated with excess ozone at −78° C. Diisopropylethylamine (11.5 mL, 66.0 mmole) was then added dropwise over 30 min and the mixture allowed to come to room temperature and stir overnight under a nitrogen atmosphere. The mixture was then diluted to 600 mL with methylene chloride, washed three times with 100 mL portions of 2N HCl (aq), twice with 200 mL portions of saturated aqueous sodium bicarbonate and with 200 mL of saturated brine. The solution was dried over magnesium sulfate, filtered and concentrated in vacuum to a crude brown oil, which was column chromatographed on silica gel with 10% hexane/ methylene chloride to give 7.52 g of the (R)-enantiomer of the title compound as a yellow solid. $^1$H-NMR (CDCl$_3$): doublet 7.8 δ (2H); doublet 7.62 δ (1H); doublet 7.4 δ (2H); doublet 7.0 δ (1H); multiplet 4.4–4.6 δ (2H); multiplet 4.2 δ (3H); singlet 2.4 δ (3H).

INTERMEDIATE 12

Toluene-4-sulfonic Acid 7-Nitro-8-(2-nitro-but-1-enyl)-2,3-dihydro-benzo[1,4]dioxin-2-ylmethyl Ester To a solution of 1.0 g (2.45 mmole) of (2R)-(8-formyl-7-nitro-2,3-dihydro-1,4-benzodioxin-2-yl)methyl 4-methylbenzenesulfonate in 15 mL of acetic acid was added 0.87 mL (9.8 mmole) of nitropropane and 0.38 g (4.9 mmole) of ammonium acetate and the mixture was heated at 80° C. under nitrogen for 6 hours. After the mixture cooled, the solvent was removed in vacuum and replaced with 200 mL of ethyl acetate. The solution was washed with 200 mL of water and the aqueous wash was back-extracted with an additional 200 mL of ethyl acetate. The combined organics were washed with 200 mL each of saturated aqueous sodium bicarbonate and saturated brine, dried over magnesium sulfate, filtered and concentrated in vacuum to an oily yellow solid. Column chromatography on silica gel with 1:1 hexane/ethyl acetate as eluant gave 0.70 g of the (R)-enantiomer of the title compound as a yellow solid. $^1$H-NMR (CDCl$_3$): doublet 7.8 δ (2H); doublet 7.75 δ (1H); doublet 7.4 δ (2H); doublet 7.03 δ (1H); singlet 5.3 δ (1H); multiplet 4.45 δ (1H); multiplet 4.4 δ (1H); multiplet 4.21 δ (3H); singlet 2.45 δ (3H); quartet 2.4 δ (2H); triplet 1.0 δ (3H).

INTERMEDIATE 13

[8-Ethyl-2,3-dihydro-7H-[1,4]dioxino[2,3-e]indol-2-yl]methyl 4-Methylbenzenesulfonate 0.70 g (1.5 mmole) of toluene-4-sulfonic acid (2R)-7-nitro-8-(2-nitro-but-1-enyl)-2,3-dihydro-benzo[1,4]dioxin-2-ylmethyl ester was dissolved in 100 mL of ethyl acetate and 0.10 g of platinum oxide added. The mixture was treated with 45 psi of hydrogen on a Parr hydrogenation apparatus for 5 hours. The mixture was then filtered through celite and concentrated in vacuum. The residue was column chromatographed on silica gel with 1:1 ethyl acetate/hexane to give 0.52 g of the (R)-enantiomer of the title compound as a yellow oil. $^1$H-NMR (CDCl$_3$): doublet 7.8 δ (2H); doublet 7.3 δ (2H); doublet 6.76 δ (1H); doublet 6.64 δ (1H); singlet 6.16 δ (1H); multiplet 4.5 δ (1H); multiplet 4.3 δ (3H); quartet 4.1 δ (1H); quartet 2.75 δ (2H); singlet 2.5 δ (3H); triplet 1.3 δ (3H).

EXAMPLE 4

8-Ethyl-2-[(4-(1H-indol-3-yl)-3,6-dihydropyridin-1(2H)-yl)methyl]-2,3-dihydro-7H-[1,4]dioxino[2,3-e]indole A solution of 0.52 g (1.3 mmole) of [(2R)-8-ethyl-2,3-dihydro-7H-[1,4]-dioxino[2,3-e]indol-2-yl]methyl 4-methylbenzenesulfonate and 0.80 g (4.1 mmole) of 3-(1,2,3,6-tetrahydro-4-pyridinyl)-1H-indole in 20 mL of DMSO was heated at 65° C. for 3 hours. The mixture was diluted with 300 mL of ethyl acetate, washed with 200 ml portions of saturated aqueous sodium bicarbonate and saturated brine, dried over magnesium sulfate, filtered and concentrated in vacuum. The residue was column chromatographed on silica gel with 0–2% methanol in methylene chloride as eluant. The product fractions were combined and concentrated in vacuum, and the residue triturated with ether/hexane (1:1) to give 0.11 g of the (S)-enantiomer of the title compound as a yellow solid hydrate, m.p. 175–177° C.

Elemental Analysis for: C$_{26}$H$_{27}$N$_3$O$_2$.H$_2$O; Calc'd: C, 72.37; H, 6.77; N, 9.74. Found: C, 72.67; H, 6.63; N, 9.62.

EXAMPLE 5

8-Ethyl-2-[(4-(5-fluoro-1H-indol-3-yl)-3,6-dihydropyridin-1(2H)-yl)methyl]2,3-dihydro-7H-[1,4]dioxino[2,3-e]indole A solution of 0.41 g (0.1.1 mmole) of [(2R)-8-ethyl-2,3-dihydro-7H-[1,4]-dioxino[2,3-e]indol-2-yl]methyl 4-methylbenzenesulfonate and 0.71 g (3.3 mmole) of 5-fluoro-3-(1,2,3,6-tetrahydro-4-pyridinyl)-1H-indole in 25 mL of DMSO were heated at 75–80° C. for 4 hours. The mixture was diluted with 300 mL of ethyl acetate, washed with 200 ml portions of saturated aqueous sodium bicarbonate and saturated brine, dried over magnesium sulfate, filtered and concentrated in vacuum. The residue was column chromatographed on silica gel with 0–2% methanol in methylene chloride as eluant. The product fractions were combined and concentrated in vacuum, and the residue triturated with ether/hexane (1:1) to give 0.090 g of the (S)-enantiomer of the title compound as a yellow solid hydrate, m.p. 81–82° C.

Elemental Analysis for: C$_{26}$H$_{26}$FN$_3$O$_2$.H$_2$O; Calc'd: C, 69.47; H, 6.28; N, 9.35. Found: C, 69.72; H, 6.30; N, 9.25.

What is claimed is:

1. A method of inhibiting the reuptake of serotonin in a subject suffering from a condition selected from the group consisting of post-traumatic stress disorder, premenstrual dysphoric disorder, attention deficit disorder, obesity, eating disorders, vasomotor flushing, cocaine and alcohol addiction, and sexual dysfunction, which comprises providing to the subject suffering from said condition, a serotonin selective reuptake inhibitory effective amount of a compound of formula I

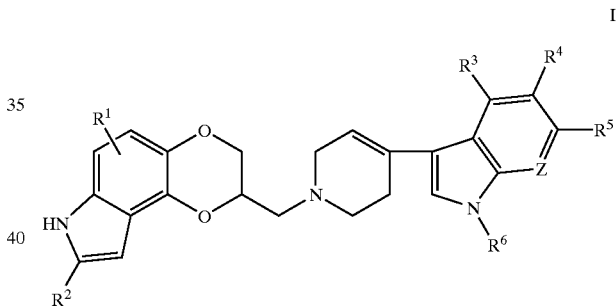

wherein $R^1$, $R^3$, $R^4$, $R^5$ and $R^7$ are, independently, hydrogen, halo, cyano, carboxamido, carboalkoxy of two to six carbon atoms, trifluoromethyl, alkyl of 1 to 6 carbon atoms, alkoxy of 1 to 6 carbon atoms, alkanoyloxy of 2 to 6 carbon atoms, amino, mono- or di-alkylamino in which each alkyl group has 1 to 6 carbon atoms, alkanamido of 2 to 6 carbon atoms, or alkanesulfonamido of 1 to 6 carbon atoms;

$R^2$ is hydrogen, halogen, alkyl of 1 to 6 carbon atoms or trifluoromethyl;

$R^6$ is hydrogen or alkyl of 1 to 6 carbon atoms;

Z is $CR^7$ or N;

or a pharmaceutically acceptable salt thereof.

2. The method of claim 1 wherein the subject is a human.

* * * * *